(12) United States Patent
Tannahill et al.

(10) Patent No.: US 8,667,969 B2
(45) Date of Patent: Mar. 11, 2014

(54) POSITIONER DEVICE

(76) Inventors: David Bruce Tannahill, Merriam, KS (US); Kristi Lynn Tannahill, Merriam, KS (US)

( * ) Notice: Subject to any disclaimer, the term of this patent is extended or adjusted under 35 U.S.C. 154(b) by 94 days.

(21) Appl. No.: 12/925,854

(22) Filed: Nov. 1, 2010

(65) Prior Publication Data

US 2011/0100375 A1     May 5, 2011

Related U.S. Application Data

(60) Provisional application No. 61/280,136, filed on Oct. 31, 2009.

(51) Int. Cl.
*A61G 15/00* (2006.01)

(52) U.S. Cl.
USPC ........... 128/845; 128/848; 128/871; 128/876; 5/636; 5/639; 5/640; 5/646; 5/650

(58) Field of Classification Search
USPC ........... 128/845, 848, 871, 876; 2/425; 5/636, 5/639, 640, 646–647, 650; 606/204.15
See application file for complete search history.

(56) References Cited

U.S. PATENT DOCUMENTS

| | | | |
|---|---|---|---|
| 876,491 A * | 1/1908 | Rohwer | 128/871 |
| 3,946,451 A | 3/1976 | Spann | |
| 4,796,315 A * | 1/1989 | Crew | 5/630 |
| 5,199,124 A * | 4/1993 | Klemis | 5/630 |
| 5,909,733 A | 6/1999 | Ehrich | |
| 6,305,039 B1 | 10/2001 | Jenkins et al. | |
| 6,311,346 B1 * | 11/2001 | Goldman | 5/81.1 T |
| 6,357,444 B1 * | 3/2002 | Parker | 128/848 |
| 7,150,057 B1 | 12/2006 | Santiago et al. | |
| 2008/0223376 A1 * | 9/2008 | Delaplane et al. | 128/845 |

* cited by examiner

*Primary Examiner* — Patricia Bianco
*Assistant Examiner* — Caitlin Carreiro
(74) *Attorney, Agent, or Firm* — Husch Blackwell LLP

(57) ABSTRACT

A foam positioner device utilized for maintaining resting limb positioning, hand shape and strength therapies, and other modality therapies. Said device, by means of an integrated strap slot base, incorporates a generic strap which wraps around furnishings such as pillows, recliner footrests, beds, chairs, and various medical apparatus exclusively and does not attach to the person.

21 Claims, 4 Drawing Sheets

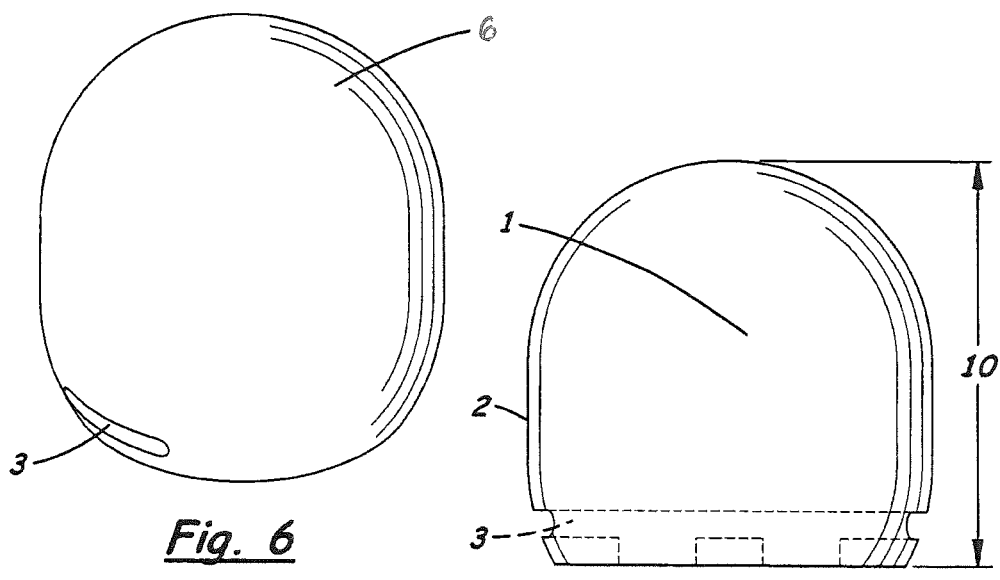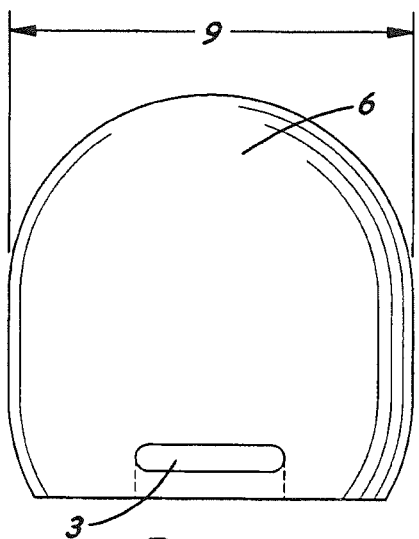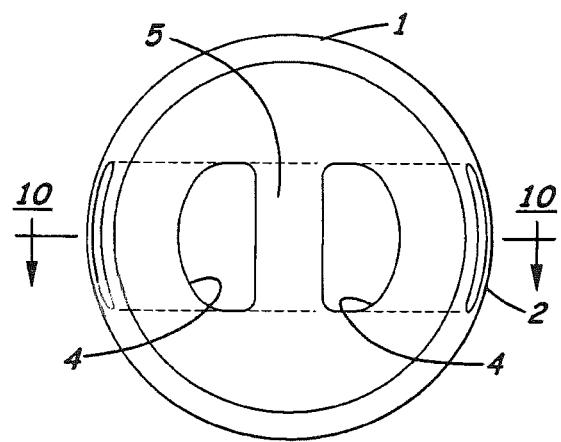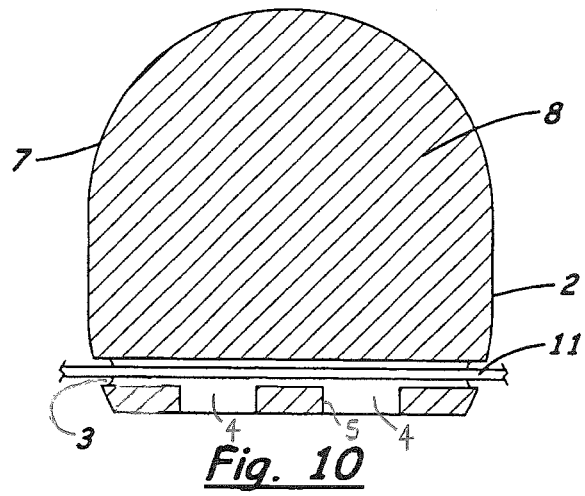

POSITIONER DEVICE

CROSS REFERENCES TO RELATED APPLICATIONS

This is a non-provisional patent application from a provisional patent application filed on Oct. 31, 2009, Application No. 61/280,136

STATEMENT REGARDING FEDERALLY SPONSORED RESEARCH OR DEVELOPMENT

Not applicable

THE NAMES OF THE PARTIES TO A JOINT RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention, a type of medical positioner device, comprises a device for maintaining limbs and appendages in a desired, consistent position and place so as to improve comfort, limit or control rotation (both internal and external rotation), and control movement (adduction and/or abduction), not "fall" (e.g. drop down) from an elevated position, or otherwise impede the healing process, and for providing consistent shape and location for various limb and appendage therapies. Said device is positioned in proximity to a limb and is not attached to the person in any way, but is only attached to the furnishings, etc., by means of a strap(s) fastened through the integrated strap slot base.

2. Description of the Prior Art

This device is like nothing to be found, as far as we have been able to find, to the current date. However, there are a few patents issued for other devices that have to do indirectly with the function of this device. The functions of these other devices are completely different and apart from the function of the present device, but they are listed below.

A prior art device invented by Santiago and Santiago, U.S. Pat. No. 7,150,057, named "Lower Leg and Foot Support," comprises a pillow made for leg and foot support. This device is different in that the patient's legs or feet are placed directly onto the pillow which then functions principally for elevation. Nothing is provided to prevent movement or to maintain position, as in the present device, and application is limited to the lower limb.

Another prior art device, invented by Donald C. Spann, U.S. Pat. No. 3,946,451, named "Limb Support," comprises a polyurethane foam support that cradles a limb on top of said device. The device invented by Spann is different because the application of said device is limited to lower extremities only, said device is not strapped in place, the device has only the extremity resting upon it exclusively—not either upon or beside, and it does not have an integrated covering within the foam material.

The next prior art device, invented by Jenkins and Svensson, U.S. Pat. No. 6,305,039 B1, named "Resting System," comprises a system to rest the entire body on to prevent pressure sores. Said device is complicated and large with many pieces, wherein the present device is simple, easily moveable and lightweight, and interfaces with many different furnishings both large and small.

The present device provides many of the same benefits as the device of Jenkins and Svensson for the prevention of bed sores but the present device does so in a much broader application in an easier to use and simpler manner. The present device is particularly needed as modern hospital beds have bed sore prevention systems already built into the 'mattress' but do not provide the positioning benefits of present device.

Another prior art device, invented by Keith Ehrich, U.S. Pat. No. 5,909,733, named "Mechanism for Securing a Patient's Limb," comprises a flat-surfaced, padded device made to be attached to the rails on the side of a hospital-type bed. This device is different because it has no straps, is not readily portable nor easily moveable, and has a very limited range of applications being dependent upon the design of various bed rails. The present device would interface with said device to aid in positioning of a limb during a medical procedure thus providing the consistent positioning that said device lacks being only able to provide elevation and generalized positioning.

BRIEF SUMMARY OF THE INVENTION

The present device is a type of foam cushion that remains in place because the base has an integrated strap slot. A common strap fastens through the slot and wraps around furnishings which makes it possible for the present device to not move when a limb rests beside or upon it. This provides substantial benefits for resting upper or lower limbs and for various appendage therapy treatments.

The present device, by virtue of not being a restraint, is very practical because the person is free to move their limb(s), even leaving and then returning to the furnishings, with the present device remaining positioned as it was previously. This is practical for ambulatory patients or for medical equipment with different patients. The present device provides a comfortable and consistent means for limbs to be positioned.

The present device adds benefits to care givers as well, in that present device provides consistent positioning for patients. Other common positioners, such as pillows, inadvertently move out of position or do not adequately support a limb without constant adjustment. This is particularly acute when attempting to support a lower limb on a pillow placed on a bed or a footrest of a recliner after a medical procedure such as a joint replacement or when dealing with bulky casts, splints, or braces.

BRIEF DESCRIPTION OF THE DRAWINGS

FIG. 6 depicts a Perspective View of a medical or position device

FIG. 7 depicts a Side View of a medical or position device.

FIG. 8 depicts an End View a medical or position device.

FIG. 9 depicts a Bottom View of a medical or position device.

FIG. 10 depicts a Cross Section or Cut View of a medical or position device with a Generic Strap placed straight through Integrated Strap Slot.

DETAILED DESCRIPTION OF INVENTION

Figure 1:
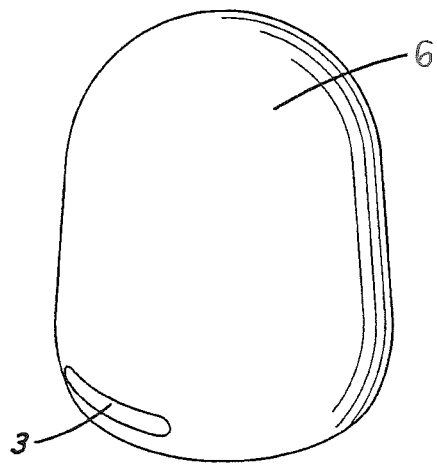
FIG. 1 depicts a Perspective View of a medical or position device.
Figure 2:
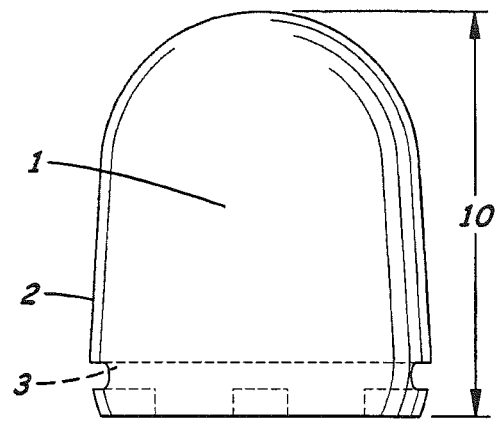
FIG. 2 depicts a Side View of a medical or position device.
Figure 3:
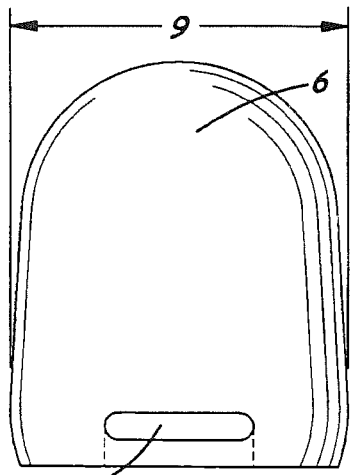
FIG. 3 depicts an End View of a medical or position device.

The present invention, a type of medical positioner device, comprises a device for maintaining limbs and appendages in a desired, consistent position and place so as to improve comfort, limit or control rotation (both internal and external rotation), and control movement (adduction and/or abduction), not "fall" (e.g. drop down) from an elevated position, or otherwise impede the healing process, and for providing consistent shape and location for various limb and appendage therapies. Said device is positioned in proximity to a limb and is not attached to the person in any way, but is only attached to the furnishings, etc., by means of a generic strap 11 fastened through the integrated strap slot 3 base. The body 6 of the device can be positioned in many different ways, as a single unit or in multiples, on the same generic strap 11 or separate generic straps 11, such that the integrated strap slot 3 can be secured to the pillow, bed, footrest area of a chair (e.g. the footrest of a recliner or the area for limbs on a medical procedure chair or table or dental chair), or other such thing said person is lying, sitting, or resting upon (e.g. pillow may be in lap for arm), thus providing a stationary mechanical block for limbs preventing or controlling movement or rotation, stabilizing a limb that may have various types of footwear, a cast, splint, brace, stump, fixator, or prosthesis, or other such corrective or surgical device; protecting a limb with wounds, injuries, or skin breakdown, providing support and alignment for limbs, related joints, and extremities at rest; while also allowing ambulation, as relevant.

Additionally, on emergency medical gurneys, medical testing machinery, or other positions with transport or movement surfaces that utilize separate strapping devices to "hold" a person in position, the present device provides a surface for the "other strap" to rest upon, thereby gaining elevation and distance away from the person's limb or limbs. This is relevant in such settings where the person's limbs would be made uncomfortable by the "other strap" having multiple points of contact. Surfaces that normally have direct contact with the skin, such as sheets and bedding materials, when lying in bed, can also be "held off" e.g. above the limbs, aiding in comfort and healing to damaged skin.

The present device, being spherical or cylindrically spherical, can not only aide in various modality therapies by assisting with positioning, but also in such functions as a "stationary ball." Balls such as "stress balls" or "exercise balls" are commonly associated with Occupational or Physical Therapy for hand strengthening after a stroke, surgery, or injury. Said device functions for the hand, as well as other parts of the body as relevant, as a stationary or semi-stationary "stress or exercise ball" or cylinder at a fixed location on or over a travel path of a portion of the generic strap 11. The present device, as a stationary or semi-stationary ball, additionally provides consistent location for various other treatments and therapies such as "Trigger Point Therapy" that uses a ball such as a tennis ball between the person's body and such surfaces as a bed or the back of a chair. Said device provides the function of various balls or cylinders, but adds the consistent or steady location without falling down or out of position.

The diameter of the current device ranges 2.0 to 8.0 inches. Said device is fabricated from foam products such as self-skinning molded polyurethane that feels like vinyl-covered foam, such that the side 1, or end 2, outer surface 7, and core 8 are of an appropriate texture and density for comfort and function when set against the person's limb or otherwise utilized. The "density representative number," indicates the relative density or firmness of the body 6 of said devices. This number is between one and ten and is molded into the bottom of said device, in an area where there is no finger hole 4, see FIG. 4 and FIG. 9. The outer surface 7 of the present device is relatively smooth, comfortable, and impervious to most liquids.

The present device can be made with the diameter 9 and the height 10 either equal, where the ratio of diameter to height is 1:1, as in FIG. 6 through FIG. 10; or unequal where the ratio of diameter to height is within the range of 1:1 to 1:8, as illustrated in FIG. 1 through FIG. 5, where the diameter to height ratio is 1:1.2. The basic function of said device is the same, but different uses may need different diameter 9 and height 10 ratios.

Figure 4:
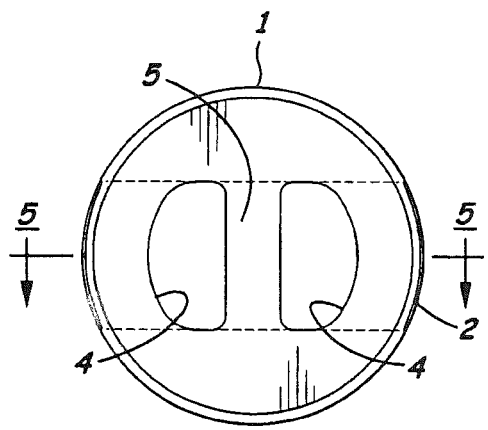
FIG. 4 depicts a Bottom View of a medical or position device.
Figure 5:
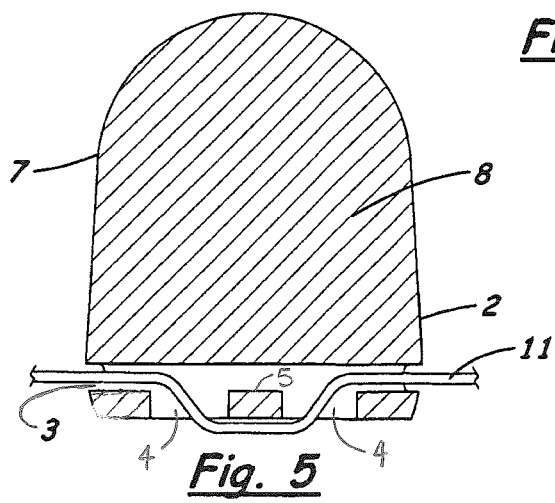
FIG. 5 depicts a Cross Section or Cut View of a medical or position device with a Generic Strap woven through the Integrated Strap Slot Weaving Section.
Figure 11:
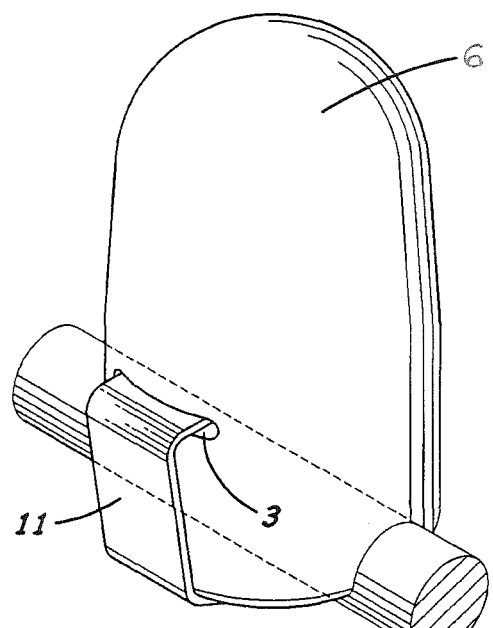
FIG. 11 depicts a Perspective View of the invention attached to a Wheelchair Leg Rest Extension or other furnishing rail.
Figure 12:
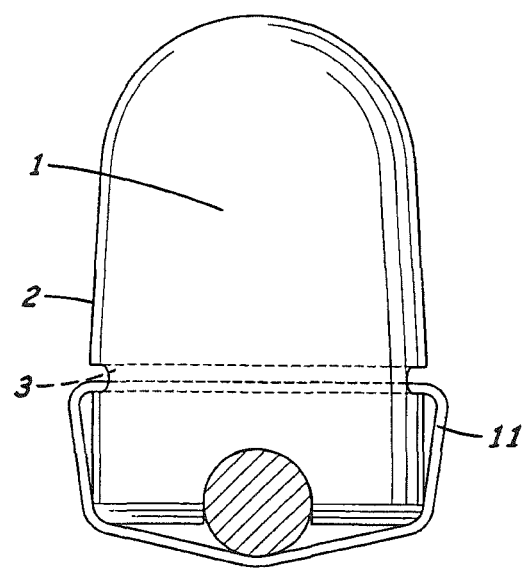
FIG. 12 depicts a Side View of the invention attached to a Wheelchair Leg Rest Extension or other furnishing rail.
Figure 13:
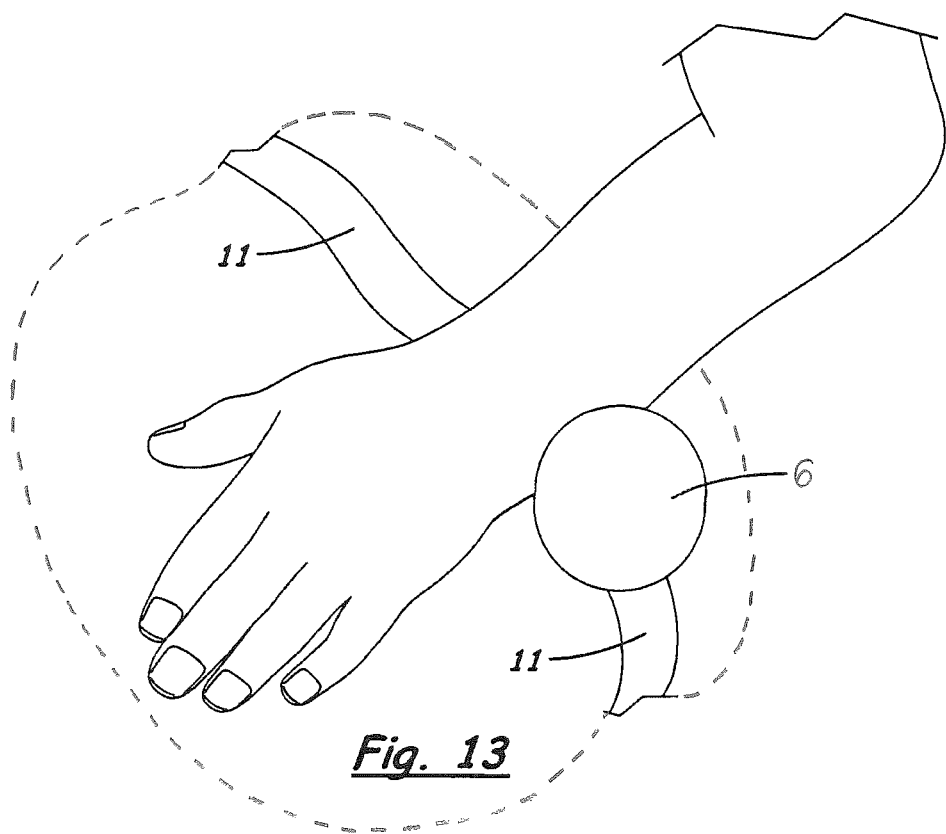
FIG. 13 depicts a Perspective View of the invention illustrating how it can be used to maintain positioning of a forearm.
Figure 14:
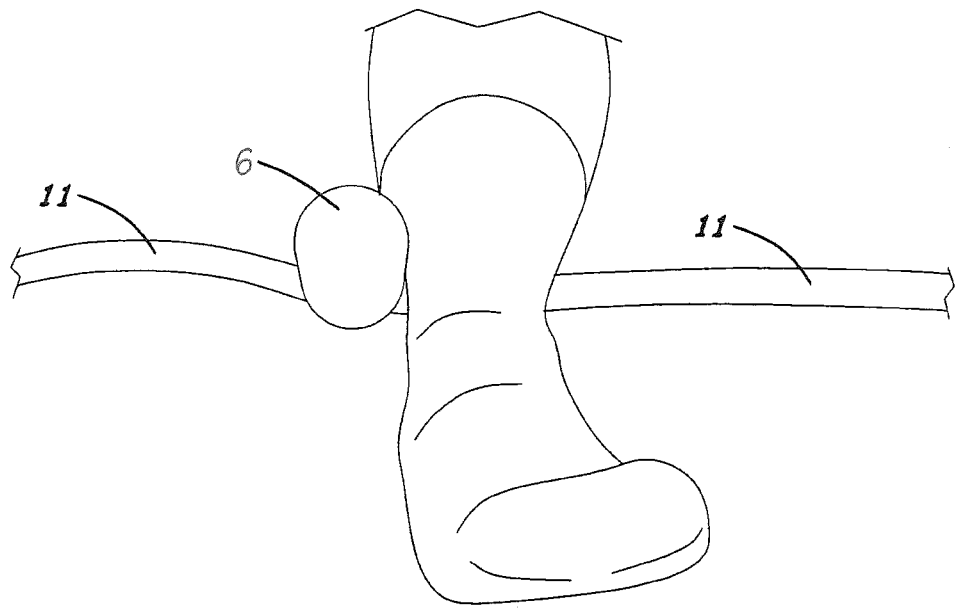
FIG. 14 depicts a Perspective View of the invention illustrating how it can be used to maintain positioning of a lower leg.

The bottom views, FIG. 4 and FIG. 9, of present device show the back to back 'D-shaped' finger holes 4 that facilitate the generic strap 11 to be fed straight through the strap slots 3 so as to go out the other end 2, through the strap slot 3 on the opposite end 2 of the device, FIG. 10, thus providing a semi-fixed position. Furthermore, the 'D-shaped' finger holes 4 can also be utilized so as to 'weave' the generic strap 11 through the strap slot 3, over the strap slot weaving section 5 of the back to back 'D-shaped' finger holes 4, and out through the strap slot 3 on the opposite end 2 of the device, FIG. 5, thus providing a fixed position for said device.

The generic strap 11, having a tensioning buckle at one end, is made from readily available materials such as web strap or VELCRO™ (hook-and-loop fastener) type double faced loop-only strapping, utilized for skin comfort, with sewn on hook patches, or other available strapping materials. The generic strap 11 quantity for present device, though many times only one, is proportionate to the overall size and shape of present device. The generic strap 11 width size may range from 1" to 2" generally being proportionate to the diameter 9 of said device, e.g. diameters 9 greater than 3" may utilize 1.5" or 2" wide straps, therefore the size of the strap slot 3 will be proportionate to the generic strap 11 width.

Other related materials may or may not be used in combination with the present device including disposable or washable coverings for the said device that function as a "sock or sleeve" to provide additional comfort, cleanliness, or wound care management.

KEY TO FIG. 1 THROUGH FIG. 14

1—Side
2—End
3—Strap Slot
4—Finger Hole(s)
5—Strap Slot Weaving Section
6—Body
7—Outer Surface
8—Core
9—Diameter 10—Height
11—Generic Strap

We claim:

1. A positioner device, said device comprising:
   a body having a bottom surface, a top surface, a first end opposite a second end, and a height defined between said top and bottom surfaces;
   a slot defined through and extending from the first end to the second end of said body, said slot positioned proximate said bottom surface and being configured for receiving a strap at least partially therethrough;
   first and second holes defined through said bottom surface, said first and second holes extending to and intersecting said slot, a portion of said body being located above said first and second holes; and
   a weaving section located between said first and second holes;
   wherein said slot is positioned above said first and second holes and said first and second holes terminate within said slot.

2. The device of claim 1 configured such that a strap is selectively integrated therewith in a first orientation for retaining said device in a semi-stationary position or a second orientation for retaining said device in a stationary position.

3. The device of claim 1 further comprising a strap, said strap passing directly through said slot for retaining said device in a semi-stationary position.

4. The device of claim 1 further comprising a strap, said strap being weaved through said first and second holes for retaining said device in a stationary position.

5. The device of claim 1 further comprising a strap, said strap passing through a first end of said slot, through said first hole, around said weaving section, through said second hole and through a second end of said slot for retaining said device in a stationary position.

6. The device of claim 1, wherein said first and second holes perpendicularly intersect with said slot.

7. The device of claim 1, wherein said slot is defined in a horizontal direction and said first and second holes are each defined in a vertical direction.

8. The device of claim 1, wherein said first and second holes are D-shaped finger holes to facilitate a strap being fed through said slot.

9. The device of claim 1, wherein said body is spherical or cylindrical.

10. The device of claim 1, wherein said body includes a dome-shaped top.

11. The device of claim 1, wherein said bottom surface is flat.

12. The device of claim 1, wherein said body has a diameter of between 2" and 5".

13. The device of claim 12, wherein a ratio of said diameter to said height is between about 1:1 and about 1:8.

14. The device of claim 1, wherein said body is formed of a molded polyurethane foam.

15. The device of claim 1, wherein said device is attached to a furnishing and not attached to a person.

16. The device of claim 1, wherein said device is configured for limiting a range of movement or maintaining a position of a limb or appendage.

17. A positioner device, said device comprising:
    a body having a bottom surface, a top surface, a first end opposite a second end, and a height defined between said top and bottom surfaces;
    a slot defined through and extending from the first end to the second end of said body, said slot positioned proximate said bottom surface and being configured for receiving a strap at least partially therethrough; and
    at least one hole defined through said bottom surface, said at least one hole extending to and intersecting said slot, a portion of said body being located above said at least one hole;
    wherein said slot is positioned above said at least one hole and said at least one hole terminates within said slot.

18. The device of claim 17 further comprising a strap, said strap passing directly through said slot.

19. The device of claim 17 further comprising a strap, said strap passing through a first end of said slot and exiting through said at least one hole.

20. The device of claim 1, wherein said body has a cylindrical shape defined by a diameter and said height and an outer surface of a curved side of said body is suitable for supporting a limb or appendage.

21. The device of claim 1 further comprising a strap, wherein said strap may optionally be passed either directly through said slot for retaining said device in a semi-stationary position or weaved through said slot and said first and second holes for retaining said device in a stationary position.

* * * * *